(12) United States Patent
Guzzo et al.

(10) Patent No.: US 6,623,462 B2
(45) Date of Patent: Sep. 23, 2003

(54) NEEDLE SAFETY GUARD

(75) Inventors: Michael Guzzo, West Seneca, NY (US); Robert P. Michaloski, Hamburg, NY (US); Michael J. Murphy, Co. Cork (IE)

(73) Assignee: Harmac Medical Products, Inc., Buffalo, NY (US)

( * ) Notice: Subject to any disclaimer, the term of this patent is extended or adjusted under 35 U.S.C. 154(b) by 0 days.

(21) Appl. No.: 10/124,501

(22) Filed: Apr. 17, 2002

(65) Prior Publication Data

US 2002/0169425 A1 Nov. 14, 2002

Related U.S. Application Data

(60) Provisional application No. 60/290,331, filed on May 11, 2001.

(51) Int. Cl.[7] .......................... A61M 5/00; A61M 5/32
(52) U.S. Cl. ...................................... 604/263; 604/177
(58) Field of Search ............................ 604/263, 177, 604/192, 198, 110, 164.08, 162

(56) References Cited

U.S. PATENT DOCUMENTS

| | | | |
|---|---|---|---|
| 3,310,051 A | | 3/1967 | Schulte |
| 4,627,843 A | * | 12/1986 | Raines ........................ 604/263 |
| 4,631,058 A | | 12/1986 | Raines |
| 4,733,661 A | | 3/1988 | Palestrant |
| 4,917,243 A | * | 4/1990 | Abrams et al. .............. 604/263 |
| 5,017,189 A | * | 5/1991 | Boumendil ................. 604/192 |
| 5,046,612 A | * | 9/1991 | Mostarda et al. ........... 604/263 |
| 5,078,693 A | * | 1/1992 | Shine ......................... 604/192 |
| 5,147,319 A | * | 9/1992 | Ishikawa et al. ............ 604/174 |
| 5,167,629 A | | 12/1992 | Vertenstein et al. |
| 5,192,275 A | | 3/1993 | Burns |
| 5,279,588 A | | 1/1994 | Nicoletti et al. |
| 5,290,255 A | | 3/1994 | Vallelunga et al. |
| 5,330,438 A | | 7/1994 | Gollobin et al. |
| 5,352,204 A | | 10/1994 | Ensminger |
| 5,385,556 A | * | 1/1995 | Wang et al. ................. 604/192 |
| 5,460,612 A | | 10/1995 | Madore |
| 5,486,163 A | * | 1/1996 | Haynes ....................... 604/192 |
| 5,498,241 A | * | 3/1996 | Fabozzi ...................... 604/177 |
| 5,571,092 A | | 11/1996 | Thompson |
| 5,613,945 A | | 3/1997 | Cai et al. |
| 5,690,645 A | | 11/1997 | Van Erp |
| 5,695,470 A | | 12/1997 | Roussigne et al. |
| 5,755,694 A | | 5/1998 | Camus |
| 5,879,330 A | | 3/1999 | Bell |
| 5,921,969 A | | 7/1999 | Vallelunga et al. |
| 5,951,522 A | | 9/1999 | Rosato et al. |
| 5,997,504 A | | 12/1999 | Bell |
| 6,074,364 A | | 6/2000 | Paul |
| 2003/0069546 A1 | * | 4/2003 | Sandstrom et al. ......... 604/263 |

FOREIGN PATENT DOCUMENTS

| | | |
|---|---|---|
| EP | 0 410 734 A1 | 1/1991 |
| EP | 0 558 162 A2 | 9/1993 |
| EP | 0 629 277 A2 | 1/1996 |
| WO | WO 00/50109 | 8/2000 |

* cited by examiner

*Primary Examiner*—Sharon Kennedy
(74) *Attorney, Agent, or Firm*—Piper Rudnick LLP

(57) ABSTRACT

A needle safety guard for use with a Huber needle assembly having a body portion and a needle including an elongated body having an elongated interior cavity, the interior cavity being defined by opposed front and rear interior surfaces of the elongated body, the elongated body having a slot opening into the interior cavity and extending substantially between end portions of the elongated body; wherein the slot of the elongated body is sized and shaped to closely and slidingly engage the Huber needle body portion and the cavity is sufficiently long to fully receive the needle therein upon sliding action of the body portion along the elongated body slot from one end portion toward another; and a stop mechanism which engages the body portion to retain the needle within the cavity.

11 Claims, 4 Drawing Sheets

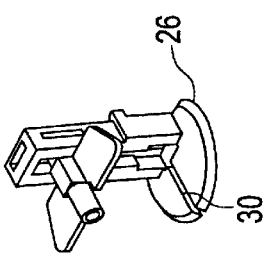
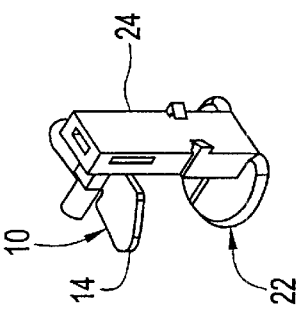
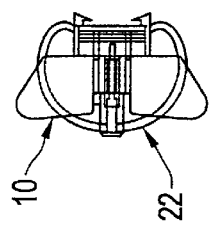
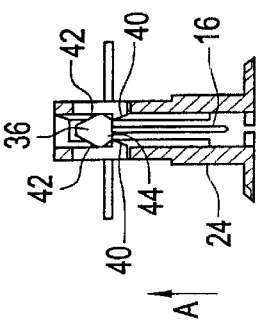
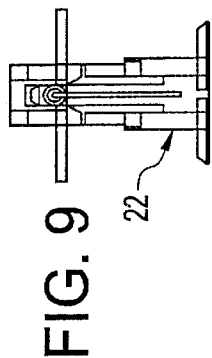
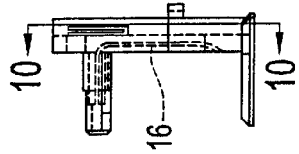
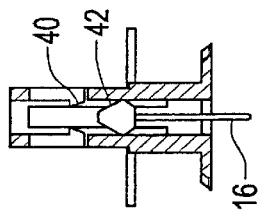
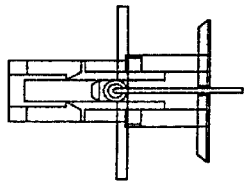
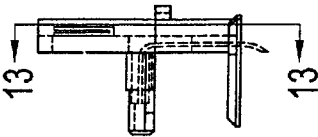

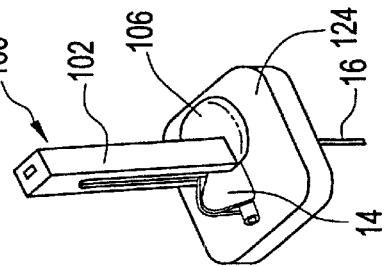
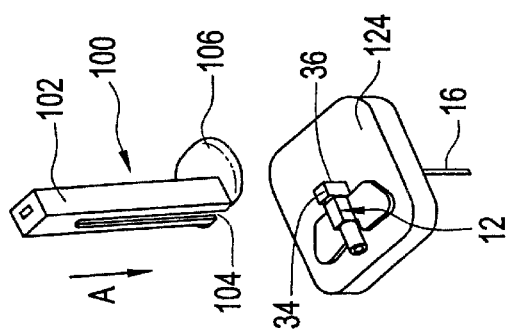
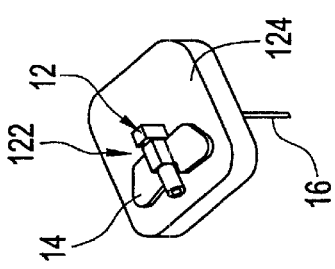
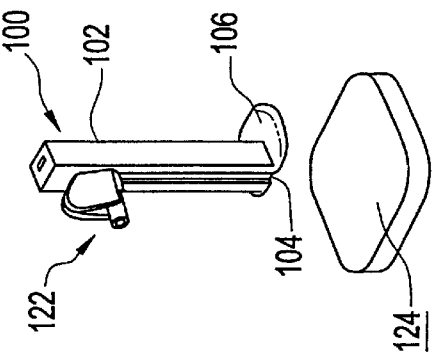
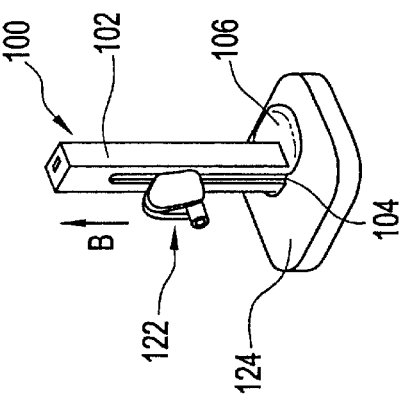

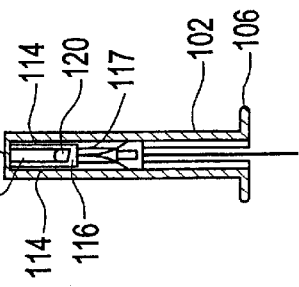
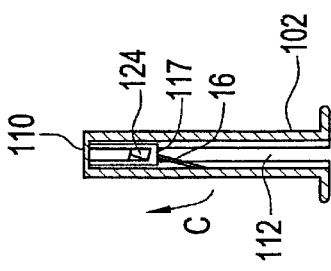
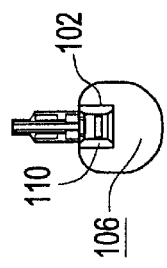
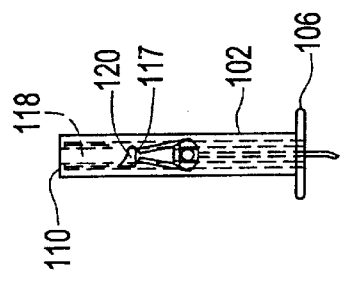
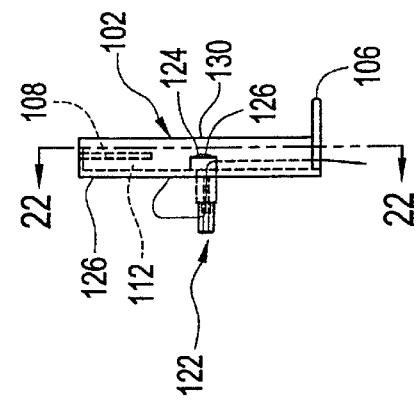
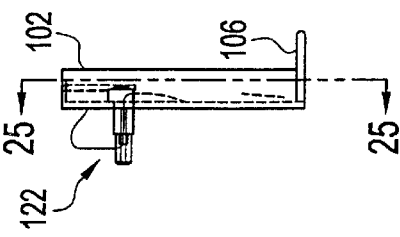

NEEDLE SAFETY GUARD

CROSS-REFERENCE TO RELATED APPLICATION

This application claims the benefit of priority to U.S. provisional patent application Ser. No. 60/290,331 filed on May 11, 2001.

FIELD OF THE INVENTION

This invention relates to a needle safety guard, particularly to an needle safety guard applicable to and intended for use in conjunction with a Huber needle with a 90° bend.

BACKGROUND

Huber needles are widely used in the medical field, typically in oncology applications in conjunction with vascular access devices, particularly those located subcutaneously.

As with other applications of needles utilized in conjunction with vascular applications, it is specially important to cover or shield used needles from the patient, other patients or healthcare providers. In that regard, it is important to provide protective measures that are not only effective, but easy to use and relatively low in cost.

SUMMARY OF THE INVENTION

A primary aspect of the invention is a needle safety guard adapted to work in conjunction with a Huber needle, the safety guard comprising a slide which covers the needle as it is extracted from the patient. The slide may be part of a clamp, a Luer connector, "y" injection site or added as an additional component clipped onto tubing, allows the needle hub to enter and slide up a track and lock into place, the lock component preventing the needle from sliding out of the track once engaged to assist in forcing the needle to stay captured in the track and not "stick" the patient or a healthcare provider.

In another aspect the invention encompasses a needle safety guard for use with a Huber needle assembly having a body portion and a needle including an elongated body having an elongated interior cavity, the interior cavity being defined by opposed front and rear interior surfaces of the elongated body, the elongated body having a slot opening into the interior cavity and extending substantially between end portions of the elongated body. The slot of the elongated body is sized and shaped to closely and slidingly engage the Huber needle body portion and the cavity is sufficiently long to fully receive the needle therein upon sliding action of the body portion along the elongated body slot from one end portion toward another. A stop mechanism engages the body portion to retain the needle within the cavity.

BRIEF DESCRIPTION OF THE DRAWINGS

FIG. 5 is a top plan view of a needle safety guard fully housing a Huber needle assembly in accordance with aspects of the invention.

FIG. 6 is a rear perspective view of the needle safety guard shown in FIG. 4.

FIG. 7 is a front perspective view of the needle safety guard shown in FIG. 4.

FIG. 8 is a side elevational view of the needle safety guard shown in FIG. 4.

FIG. 9 is a rear elevational view of the needle safety guard shown in FIG. 4.

FIG. 10 is a cross-sectional view taken along the lines A—A of FIG. 8.

FIG. 11 is a side elevational view of a Huber needle assembly engaged with a needle safety guard in accordance with the invention, the Huber needle assembly being at a position half way retracted into the needle safety guard.

FIG. 12 is a rear elevational view of the Huber needle assembly and needle safety guard shown in FIG. 11.

FIG. 13 is a cross section taken along the lines B—B of FIG. 11.

FIG. 14 is a schematic perspective view of a Huber needle in place in a patient.

FIG. 15 is a schematic perspective view of the Huber needle of FIG. 14 with another embodiment of a needle safety guard positioned above the Huber needle prior to removal of the Huber needle from the patient.

FIG. 16 is a schematic perspective view of the needle safety guard of FIG. 15 engaging the Huber needle prior to removal from the patient.

FIG. 17 is a schematic perspective view of the Huber needle and safety guard of FIG. 15 with the Huber needle substantially removed from the patient.

FIG. 18 is a schematic perspective view of the Huber needle and safety guard of FIG. 17 with the Huber needle removed completely removed from the patient and in a locked position in the safety guard.

FIG. 19 is a side elevational view of the Huber needle and safety guard of FIG. 17.

FIG. 20 is a front elevational view of the Huber needle and safety guard of FIG. 17.

FIG. 21 is a top plan view of the Huber safety needle and safety guard of FIG. 17.

FIG. 22 is a sectional view taken along the lines A—A of FIG. 19.

FIG. 23 is a side elevational view of the Huber needle and safety guard of FIG. 18.

FIG. 24 is a front elevational view of the Huber needle and safety guard of FIG. 23.

FIG. 25 is a sectional view taken along the lines B—B of FIG. 23.

DETAILED DESCRIPTION

While the invention will be described in connection with one or more preferred embodiments, it will be understood that the description is not intended to limit the invention to the described embodiments. On the contrary, the description is intended to cover all alternatives, modifications and equivalents as may be included within the spirit and scope of the invention as defined by the appended claims.

Figure 1:
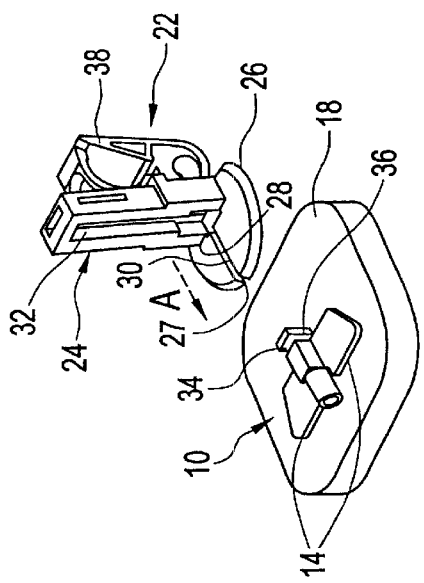
FIG. 1 is a schematic perspective view of a Huber needle prior to insertion into a portion of a patient.

Turning now to the drawings in general and FIG. 1 in particular, there is shown a Huber needle assembly 10 which includes a main body 12, a pair of butterfly wings 14, and a needle 16. The Huber needle assembly 10 is in a position to be inserted into an appropriate location on patient skin surface 18. Typically, but not always, the needle 16 is inserted into a subcutaneously located port 20.

Figure 2:
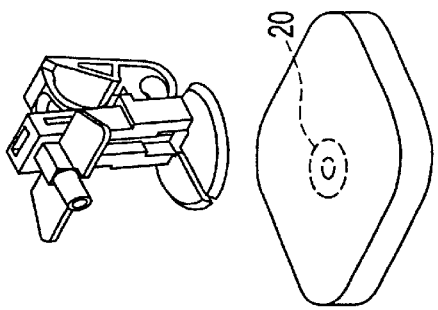
FIG. 2 is a schematic perspective view of the Huber needle of FIG. 1 in place in a patient and a needle safety guard in accordance with aspects of the invention prior to its application to the Huber needle.

In FIG. 2, Huber needle assembly 10 has been inserted into port 20 (not shown in FIG. 2) and the butterfly wings 14 are essentially parallel to and in contact with the patient's skin surface 18. FIG. 2 also shows a needle safety device 22 which includes a main body 24 and a substantially perpendicularly orientated foot 26 attached to one end portion 28 thereof. The foot 26 has a slot 30 sized and shaped to receive needle 16. Main body 24 also has a slot 32 which is sized and shaped to receive a neck portion 34. Body end portion 36 of body 12 is sized and shaped to slide within an interior cavity of main body 24 a clamp 38 is affixed to the rear side of main body 24.

Figure 3:
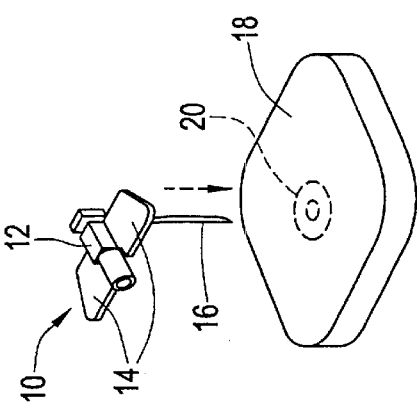
FIG. 3 is a schematic perspective view of the Huber needle located within a patient substantially as shown in FIG. 2, with the needle safety device engaging the Huber needle prior to removal from the patient.

In FIG. 2, needle safety device 22 is positioned above and slightly away from Huber needle assembly 10 and patient skin surface 18. Upon completion of the task to be performed by Huber needle assembly 10 and just prior to complete removal of needle 16 from port 20, Huber needle assembly 10 is separated slightly from surface 18 in an amount sufficient to permit foot 26 to slide between butterfly wings 14 and surface 18. This is shown in FIG. 3. In so doing, it is necessary to align needle 16 with slot 30. Needle slot 30 extends from a front opening 27 on the left side to a rear opening 28 of slot 30 on the right side (as shown in FIG. 2). As needle safety device 22 is moved in the direction shown by arrow A in FIG. 2, as applied to FIG. 3, needle 16 moves through the slot 30 and end portion 36 of body 12 enters through an opening 40 in slot 32 that is sized and shaped to permit passage of end portion 36 into the interior cavity of main body 24.

Figure 4:
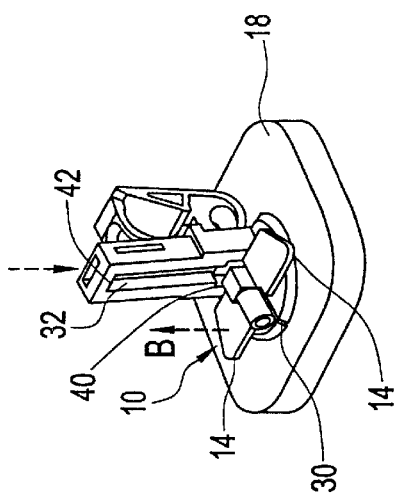
FIG. 4 is a schematic perspective view of the Huber needle assembly fully engaging the needle safety device after having been removed from the patient.

Then, Huber needle assembly 10 is moved away from surface 18 in the direction of arrow B, while retaining needle safety device 22 in position at surface 18. Neck portion 34 of body 12 is sized such that the neck portion can move from the lower portion 28 of slot 32 to an upper portion 42 of slot 32 as shown in FIGS. 4 and 5. Sliding movement along the direction of arrow B in FIG. 3 causes needle 16 to progressively move into the interior cavity of body 24 such that the distal end of needle 16 is never exposed to the patient or the healthcare provider. Subsequent to removal of Huber needle 20 from surface 18, needle 16 is fully contained within housing 24.

A ramp may also be provided at an angle to an inner surface of housing 24 which acts to bias the needle against the back surface of housing 24 such that the needle remains captured in the interior portion of body 24 and is not free in any way to come in contact with the patient or the healthcare provider.

FIGS. 5–10 show provide various views of a Huber needle assembly fully engaged with and positioned such that needle 16 of assembly 10 is fully retracted and contained within the interior cavity of main body 24.

Referring specifically to FIGS. 9 and 10, a lock mechanism comprising a pair of angled ribs 40 extend from the main body 24 sides into the interior cavity. The angled ribs 40 engage angled surfaces 42 of body end portion 36 during sliding action of assembly 10 relative to needle safety guard 22. Once the bottom surface 44 of end portion 36 passes ribs 40, assembly 10 is locked into position within needle safety guard 22 and needle 16 is locked within the interior cavity of main body 24.

FIGS. 11–13 show assembly 10 at a midpoint in its sliding action with respect to needle safety guard 22. At that point, angled ribs 40 have yet to contact angled sides 42 and assembly 10 is not yet locked into its final position.

The needle assembly and needle safety guard can be used according to the following basic guidelines:

1. Remove the needle assembly from the sealed blister tray, separating the PE tubing guard from the needle. Position the exposed needle perpendicular to the port surface. The guard is appended to the design of the thumb clamp device and does not initially restrict the access of the needle to the port.
2. Fully insert the needle into the port. Administer treatment as necessary.
3. Slide the flat end (foot) of the guard device underneath the butterfly wings and position the needle hub in the middle. Position the mating knob extending off the needle hub into the slide of the thump clamp appendage.
4. Squeeze the butterfly wings and pull out the needle from the port while stabilizing the patient surface by pressing the thumb clamp appendage down. The slide within the thumb clamp appendage guides the needle assembly.
5. The needle has been pulled completely out of the port and all the way up the slide. At the end of the slide the mating knob now becomes restricted by an internal step, making it extremely difficult to remove.

FIGS. 14–25 show another embodiment of the invention as reflected primarily in needle safety guard 100 which includes a main body 102 having a longitudinally shaped slot 104 extending from the base portion of the safety guard upwardly toward the upper portion of the safety guard. A substantially perpendicularly oriented foot 106 extends outwardly from a base portion of the safety guard in the direction opposite of the side in which the slot 104 is located. The bottom portion of the main body 102 is open, while the upper portion of main body 102 is preferably substantially closed.

Referring specifically to FIGS. 19–25, a needle assembly lock 108 is located interiorly of main body 102 and extends from the ceiling 110 of main body 102 downwardly into the inner chamber 112 of main body 102. Lock 108 has a pair of legs 114 connected to ceiling 110 and which at a lower portion of the legs connect to a lock cross member 116. The legs 114, cross member 116 and ceiling 110 form the boundaries of a lock slot 118. The uppermost surface 120 of cross member 116 is oriented at an angle relative to the upper surface of cross member 116.

Huber needle assembly 122 is substantially the same as Huber needle assembly 10 referred to with respect to FIGS. 1–13 inasmuch as the main body neck portion 34 and body end portion 36 are still present as best shown in FIG. 15. However, there is an angled locking wedge 124 extending from body end portion 36 which is particularly shown in FIG. 19. The remaining portions including the main body 12, butterfly wings 14 and needle 16 are, as mentioned above, substantially similar to those described with respect to the embodiment shown in FIG. 13.

The size and shape of locking wedge 124 and needle assembly lock 108 are sized, shaped and positioned with respect to one another such that a locking surface 126 of locking wedge 124 engages upper surface 120 of cross member 116 when needle assembly 122 is fully retracted into needle guard 100 and in a "locked" and safe position. This action is described in more detail below with respect to operation of the device.

Referring specifically to the process of removing Huber needle assembly 122 from a patient, reference is made to FIGS. 14–18 in particular. FIG. 14 shows Huber needle assembly 122 in its use position in a patient. Prior to removal of Huber needle assembly 122, safety guard 100 is placed in a position above Huber needle assembly 122 as shown in FIG. 15 and moved toward Huber needle assembly 122 in the direction shown by arrow A. As shown in FIG. 16, the foot 106 is placed against the surface 124 of the patient and the body 12 of Huber needle assembly 122 is positioned in the opening in the base of main body 102 such that body end portion 36 of main body 12 is positioned in the opening and neck portion 34 is located within slot 104 such that main body portion 36 is located interiorly of main body 102 and main body 12 of Huber needle assembly 122 is located exteriorly of main body 102. Also, butterfly wings 14 are folded upwardly and away from the patient surface 124.

Referring to FIG. 17, Huber needle assembly 122 is moved away from the patient surface 124 along slot 104 in the direction of arrow B, while maintaining foot 106 in contact with the patient. As shown in FIG. 18, when Huber needle assembly 122 is moved to an upper portion of slot 104, the Huber needle assembly 122 is then in a "locked" position within main body 102 and safety guard 100 can be removed from the patient surface 124.

Referring now to FIGS. 19–25, interior portions of the removal process are shown. FIGS. 19–22 correspond to the part of the removal process shown in FIG. 17 wherein Huber needle assembly 122 has been moved partially upwardly through slot 104 with locking wedge 124 still away from lock 108 and outside of lock slot 118.

FIGS. 23–25 correspond to the position of the safety guard 100 and Huber needle assembly 122 as shown in FIG. 18. As particularly shown in FIG. 25, locking wedge 124 has fully engaged lock 108 and is positioned within lock slot 118 such that locking surface 126 of locking wedge 124 has engaged upper surface 120 of lock 108, thereby locking Huber needle assembly 122 safely within safety guard 100. This is achieved by positioning of lock 108 sufficiently toward the wall 126 of main body 102 such that the surface 128 of locking wedge 124 engages the lower surface 117 of cross member 116 and, as locking wedge 124 is moved upwardly toward ceiling 110, deflects the lower portion of lock 108 towards sidewall 130 of main body 102 and, upon locking surface 126 clearing upper surface 120 of crossbar 116 by virtue of upper movement, "snaps" back into its original at-rest position, thereby locking Huber needle assembly 122 in its final position. Also by virtue of the angular orientation of upper surface 120, this causes a rotational movement of Huber needle assembly 122 in the direction shown by the arrow C of FIG. 25. The angular positioning of upper surface 120 of crossbar 116 is substantially calculated such that the lowermost tip portion 132 of needle 16 will forcibly engage the sidewall of main body 102 as shown in FIGS. 24 and 25. This provides a further level of safety against an accidental "stick" and further provides a means to prevent Huber needle assembly 122 from being accidentally removed from guard 100.

This invention may be embodied in other specific forms without departing from the spirit or essential attributes thereof and, accordingly, reference should be made to the appended claims, in addition to the foregoing specification, as indicating the scope of the invention.

What is claimed is:

1. A needle safety guard for use with a Huber needle assembly having a body portion and a needle comprising:

an elongated body having an elongated interior cavity, the interior cavity being defined by opposed front and rear interior surfaces of the elongated body, the elongated body having a slot opening into the interior cavity and extending substantially between end portions of the elongated body;

a foot extending substantially perpendicularly from one of the end portions and having a slot extending substantially perpendicularly away from the front interior surface such that the slot of the foot substantially aligns with the slot of the elongated body;

wherein the slot of the elongated body is sized and shaped to closely and slidingly engage the Huber needle body portion, the slot of the foot is sized to permit the needle portion to slide therethrough and the cavity is sufficiently long to fully receive the needle therein upon sliding action of the body portion along the elongated body slot from one end portion to another; and a stop mechanism to retain the needle portion within the cavity.

2. A needle safety guard for use with a Huber needle assembly having a body portion and a needle comprising:

an elongated body having an elongated interior cavity, the interior cavity being defined by opposed front and rear interior surfaces of the elongated body, the elongated body having a slot opening into the interior cavity and extending substantially between end portions of the elongated body;

wherein the slot of the elongated body is sized and shaped to closely and slidingly engage the Huber needle body portion and the cavity is sufficiently long to fully receive the needle therein upon sliding action of the body portion along the elongated body slot from one end portion toward another; and a stop mechanism which engages the body portion to retain the needle within the cavity.

3. The needle safety guard of claim 2, further comprising a foot extending substantially perpendicular to an axis extending along the elongated body and from one of the end portions in a direction away from the slot.

4. The needle safety guard of claim 2, wherein the stop mechanism comprises a lock connected to an end portion of the elongated body and extends within the elongated interior cavity and comprises a pair of elongated legs which connect to the end portion on one end and are connected to each other by a cross member on opposed ends.

5. The needle safety guard of claim 4, wherein the cross member has upper and lower surfaces and the upper surface is angled with respect to the lower surface.

6. The needle safety guard of claim 4, wherein the body portion of the Huber needle assembly has a locking wedge extending from one end which frictionally engages the upper surface of the lock.

7. The needle safety guard of claim 6, wherein engagement of the locking wedge with the upper surface of the cross member causes the Huber needle assembly to rotate, thereby causing an end portion of the needle to engage a sidewall of the elongated body.

8. The needle safety guard of claim 2, wherein the body portion of the Huber needle assembly has a neck portion sized to closely fit within and slide along the slot.

9. A needle safety guard for use with a Huber needle assembly having a body portion and a needle comprising:

an elongated body having an elongated interior cavity, the interior cavity being defined by opposed front and rear interior surfaces of the elongated body, the elongated body having a slot opening into the interior cavity and extending substantially between end portions of the elongated body;

wherein the slot of the elongated body is sized and shaped to closely and slidingly engage the Huber needle body portion and the cavity is sufficiently long to fully receive the needle therein upon sliding action of the body portion along the elongated body slot from one end portion toward another; and a stop mechanism which engages the body portion to retain the needle within the cavity, the stop mechanism comprising a lock connected to an end portion of the elongated body and extending within the elongated interior cavity, the lock comprising a pair of elongated legs which connect to the end portion of the elongated body on one end and are connected to each other by a cross member on opposed ends, the cross member having upper and lower surfaces and the upper surface being angled with respect to the lower surface, and wherein the body portion of the Huber needle assembly has a locking wedge extending from one end which frictionally engages the upper surface of the lock.

10. The needle safety guard of claim 9, wherein engagement of the locking wedge with the upper surface of the cross member causes the Huber needle assembly to rotate, thereby causing an end portion of the needle to engage a sidewall of the elongated body.

11. The needle safety guard of claim 9, wherein the body portion of the Huber needle assembly has a portion sized to closely fit within and slide along the slot.

* * * * *